United States Patent [19]

Colvin

[11] Patent Number: 4,850,971
[45] Date of Patent: Jul. 25, 1989

[54] INFUSION METHOD AND MEANS

[75] Inventor: David P. Colvin, Apex, N.C.

[73] Assignee: Triangle Research and Development Corporation, Raleigh, N.C.

[21] Appl. No.: 159,257

[22] Filed: Feb. 23, 1988

Related U.S. Application Data

[63] Continuation-in-part of Ser. No. 860,207, May 6, 1986, abandoned.

[51] Int. Cl.⁴ ............................................. A61M 5/00
[52] U.S. Cl. .................................... 604/134; 222/100
[58] Field of Search ................................ 222/99–101; 604/134, 135, 246

[56] References Cited

U.S. PATENT DOCUMENTS

| 2,690,179 | 9/1954 | Fox | 604/87 |
| 3,469,578 | 9/1969 | Bierman | 604/246 X |
| 3,640,277 | 2/1972 | Adelberg | 604/141 |
| 3,647,117 | 3/1972 | Hargest | 604/134 X |
| 3,670,926 | 6/1972 | Hill | 604/134 X |
| 4,337,769 | 7/1982 | Olson | 222/386.5 X |
| 4,557,728 | 12/1985 | Sealfon et al. | 604/134 |
| 4,626,243 | 12/1986 | Singh et al. | 604/246 X |
| 4,765,512 | 8/1988 | Bull | 222/100 |

FOREIGN PATENT DOCUMENTS

| 84308682.8 | 12/1984 | European Pat. Off. |
| 3021911 | 2/1982 | Fed. Rep. of Germany |
| 48434 | 9/1966 | German Democratic Rep. |

Primary Examiner—Dalton L. Truluck
Attorney, Agent, or Firm—Robert G. Rosenthal

[57] ABSTRACT

This invention is an infusion pump utilizing a linear roller driven by a one or more constant force springs in combination with changeable flow regulating needles to provide a constant flow, gravity independent device. The spring constant is chosen so that infusion substantially decreases should the infusion needle become dislodged from the vein and come to rest in the surrounding tissue. Also, there is a means for introduction of an anticoagulant to maintain vein access if a delay is encountered in replacement of the infusion bag.

14 Claims, 3 Drawing Sheets 4,850,971

INFUSION METHOD AND MEANS

This invention was made with Government support under Contract No. NAS 9-17578 awarded by the National Aeronautics and Space Administration. The Government has certain rights in this invention.

This is a continuation in part of United States Patent Application Serial No. 860,207 filed May 6, 1986, now abandoned.

FIELD OF THE INVENTION

This invention relates to medical appliances and more particularly to an improved method and means of infusing liquids into a patient independent of gravitational forces.

BACKGROUND OF THE INVENTION

Since the early development of methods of infusing liquids into patients, a problem of flow regulation has been encountered. The standard method that has been almost universally used is the elevated or hanging intravenous fluid bag or bottle. This method works fine in hospital environments where the patient is not being moved, but the same becomes very cumbersome when transport becomes necessary. This problem is even more acute in emergency situations where extra medical personnel are usually in short supply such as at accident scenes and even in ambulance and helicopter transport situations where vertical clearances may be inadequate.

To overcome the above mentioned problems, experimentation has been conducted utilizing mechanical pumps with constant tension springs to drive the same. Two of the most closely related devices of this type are shown in U.S. Pat. No. 3,670,926 to Hill and U.S. Pat. No. 3,647,117 to Hargest. In both of these patents, a variable clamp was used in an attempt to control the flow rate. Experimentation has shown, however, that in reality a fixed, repeatable, and known flow rate cannot be accomplished using devices of this type. Also, the methods of loading and unloading the infusion bag and attaching the devices in relationship to the patient were not adequate to make the same practical to use.

BRIEF SUMMARY OF THE INVENTION

After much research and study into the above-mentioned problems, the present invention has been developed to provide a mechanical, gravity-independent infusion means with a constant predetermined flow rate.

The above is accomplished through the use of one or more constant force springs which drive a take up drum to apply constant pressure to the infusion bag. The flow from such bag is accurately controlled by a flow regulating needle having a known orifice size. The flow rate can be changed by substitution of alternative sizes of flow regulating needles.

Additionally, the present invention is easily cocked, loaded, and when infusion has been completed, unloaded. Further, a means for automatically injecting an anticoagulant is provided to prevent loss of vein communication due to a delay in replacing an empty infusion bag which otherwise would lead to blood coagulation and blockage of the infusion needle.

In view of the above, it is an object of the present invention to provide an improved infusion means and method which is gravity independent in operation.

Another object of the present invention is to provide a relatively small, compact infusion means which is sturdy, light weight, and readily storable when not in use.

Another object of the present invention is to provide an improved infusion means into which infusion bags can be readily inserted and removed.

Another object of the present invention is to provide a mechanical infusion means in combination with a visual alarm system.

Another object of the present invention is to provide an infusion means which automatically injects a small quantity of anticoagulant into the system at a predetermined point to prevent loss of vein communication.

Another object of the present invention is to provide a means for automatically regulating pressure in an improved infusion means to prevent further infusion if the vein is lost.

Another object of the present invention is to provide a means for assuring a predetermined constant flow rate from an infusion means.

Another object of the present invention is to provide a plurality of alternative sizes of needles for regulating the flow of fluid from a constant pressure infusion means.

A further object of the present invention is to provide an infusion means which will infuse the liquid in to the vein or artery of a patient and wherein should the infusion needle become dislodged from the vein or artery, and come to rest in the surrounding tissue, infusion will automatically progressively and substantially decrease thereby eliminating the problem of bloating the surrounding tissue.

Other objects and advantages of the present invention will become apparent from a study of the following description and the accompanying drawings which are merely illustrative of such invention.

DETAILED DESCRIPTION OF THE ILLUSTRATED EMBODIMENT

Figure 1:
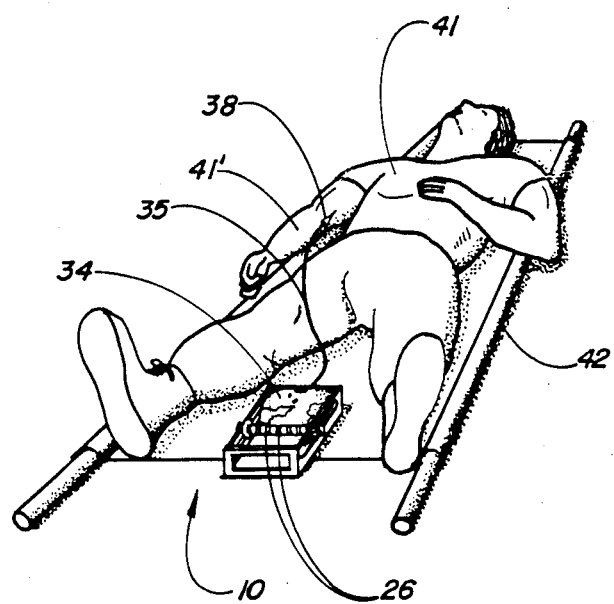
FIG. 1 is a perspective view of the improved infusion means of the present invention in an operative position relative to a patient.
Figure 2:
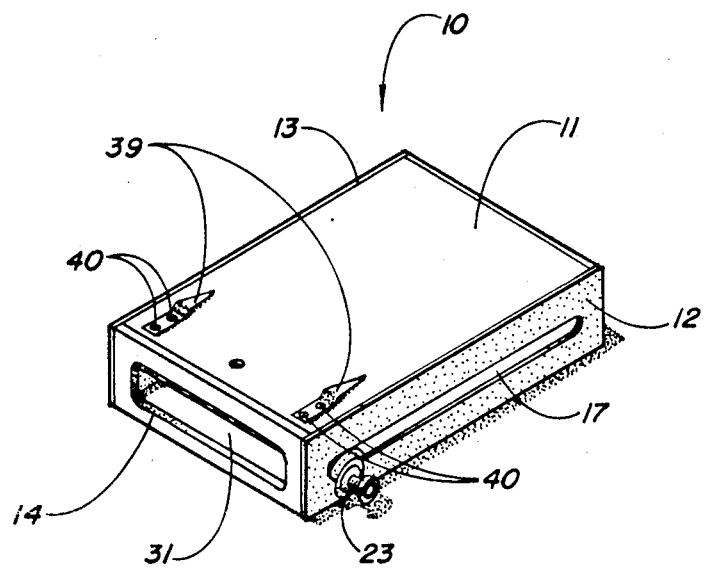
FIG. 2 is a bottom perspective view of the present invention showing the attaching clamps associated therewith.

With further reference to the drawings, the improved infusion means of the present invention, indicated generally at 10, is in the form of an open topped tray or frame means having a bottom 11 with sides 12 and 13 and ends 14 and 15 upwardly projecting from the periphery thereof. Means for securing the sides, ends and bottom can be by any securing means such as screws 16. Also, weldment could be used as well as fusion and similar methods. Such means for connecting sides, ends and bottoms of various types of materials is well known to those skilled in the art and further detailed discussion of this portion of the present invention is not deemed necessary.

Longitudinal guide slots 17 are provided in sides 12 and 13. At one end of each of these guide slots is an angulated offset slot 18 for locking the draw bar during loading of the infusion bag as will hereinafter be described.

The draw bar 19 passes axially through and mounts take up drum means 20. Guide washers 21 are provided on either end of drum 20 adjacent the interior of sides 12 and 13. Adjacent the exterior of sides 12 and 13 are guide washers 22. Cocking handles 23 are provided exteriorly of each of the washers 22 and are held in place by exterior washers 24 and draw bar engaging clips 25. Since clip-type securing means of this type are well known to those skilled in the art, further detailed discussion of the same is not deemed necessary.

The present invention obtains a constant spring force through the use of a coil type constant tension spring means or Neg'ator spring 26. This is a relatively simple device that normally consists of a storage drum and a larger diameter output drum mounted on adjacent but separate axes. The motor spring 26 itself is mounted on the storage drum 20 where it is normally free to rotate; its other end being attached to a fixed plate 27. The spring coil is pulled straight and then wound onto the output drum by bending it against its natural curvature, thereby storing energy in the spring. In this case the output drum is the IV bag itself. Only the spring material between the storage and output drums changes its stress. When the output drum is released, the spring returns to its preset form, rewinding itself on the storage drum, rotating the output drum and imparting a mechanical moment about its axis. The nearly constant torque-generated results from the spring, which has been stressed sequentially during backbending onto the output drum, releasing its energy as it returns to the storage drum.

More specifically, a plurality of constant tension coil springs 26 are secured at one end to bottom 11 by means such as spring locking plate 27 and coiled around, so as to be free floating about take up drum 20 but not otherwise secured to take up drum 20 at the other end. This particular configuration substantially lessens binding forces on the spring and drum, enhances constant fluid flow rate, and substantially simplifies the apparatus by eliminating the hardware which would otherwise be required to control binding forces which in turn degrade fluid flow rates. Plate 27 is secured to bottom 11 by means such as screws 28 and to the coil springs 26 by means such as pins 29. Since screw and pin fasteners are well known to those skilled in the art, further detailed discussion of this portion of the present invention is not deemed necessary.

The design of the above mentioned spring system is optimized to provide just enough pressure to infuse a fluid into the vein, but not enough to force a substantial amount to fluid into subcutaneous tissue or muscle. Thus, the present system is inherently safer than constant-displacement or volumetric roller pumps whose positive pressure liquid can infuse into subcutaneous tissue if the needle should inadvertently slip out of the vein. The "window" for the spring constant is defined by the venous pressure in humans which is approximately 12 cm of water pressure and the back pressure of muscle or subcutaneous tissue which is similarly known to rise significantly higher than the venous back pressure, which will be more fully described below.

The present infusion pump is designed with safety in mind; i.e., it simulates the hanging bag with its inherent safety and will not continue to infuse against a rising backpressure in excess of 70 cm-water (51 mm-Hg). More specifically, it should be understood that there is no standard figure for tissue backpressure. The backpressure associated with the tissue surrounding a vein is initially only slightly higher than the venous pressure, but will progressively increase as infusion continues to fill the intercellular space. Thus, when the infusion needle is withdrawn from a vein into the surrounding tissue, the flow will continue momentarily, but into a progressively increasing backpressure that depends upon the nature and location of that particular tissue. Infusion will therefore steadily decrease until the backpressure created by the infused liquid into the surrounding tissue space builds up to 60–70 cm of water pressure. At this point, the flow will cease unless the apparatus is purposely raised above the level of infusion to increase the differential pressure. Even then, it can only increase by the pressure head permitted by the length of the infusion catheter.

The backpressure at the infusion site is also a function of the position of the patient. Thus if the patient is standing, and infusion is into an ankle, the backpressure is already the height between the patient's heart and his ankle and the present infusion pump would probably not infuse anything; i.e., it would stall. That would not happen with a commerical roller IV infusion pump; it would keep on pumping as they typically continue to infuse even against 1000 cm of water. On the other hand, under normal circumstances, the patient will either be supine on a litter or bed or, at best, seated with his arm either at the level of the heart or slightly below it. Operating venous backpressure would be somewhere between 12 and 20 cm of water, and the present invention would be capable of operating into that window of pressure differential between 12 and 70 cm of water.

It will be noted that the present invention may easily be adapted for non-human use with equal efficacy by properly selecting the spring constant.

An opening 30 is provided in bottom 11 which can be used for mountingly securing the infusion means of the present invention to a second surface.

A hand grip opening 31 is provided in end 14 while a notch means 32 which in the illustrated embodiment is shown as a relatively deep key hole-shaped opening 32 with a bulbous lower portion is provided in end 15 for accepting the neck 33. The outer end of neck portion 33 of infusion bag 34 is adapted to receive infusion tube 35. A standard pressure clamp 36 is provided on this tube and operates in the normal manner of such devices.

A changeable, fixed orifice flow regulating needle or flow regulating means 37 is provided in the end of tube 35 opposite neck 33. Recent studies have shown that fluids containing cellular material such as blood, can be damaged by contact with rough or jagged surfaces during infusion thereby decreasing their efficacy and/or introducing the deleterious effects of clotting. In view of the foregoing, the present invention presents a smooth fluid flow path by incorporating a flow regulating means which in the illustrated embodiment is a linear, fixed orifice smooth bore flow regulating needle such as a standard infusion needle. A standard infusion needle 38 is shown in exploded fashion in FIG. 5 and is adapted to be mounted over flow regulating needle 37 when in use. Since infusion needles and their manner of mounting are well known to those skilled in the art, further detailed discussion of the same is not deemed necessary.

On the exterior of bottom 11 is provided a pair of clips formed from spring steel or similar material. These clips are secured to said bottom by means such as screws or rivits 40. These clips are specifically designed to allow the infusion means 10 of the present invention to be secured to a litter such as that shown in FIG. 1.

To use the improved infusion means of the present invention, with the patient 41 lying on a litter or similar means 42, such infusion means is clipped thereonto as shown in FIG. 1 to assure pressure head regulation relative to the point of infusion.

Figures 3, 4:
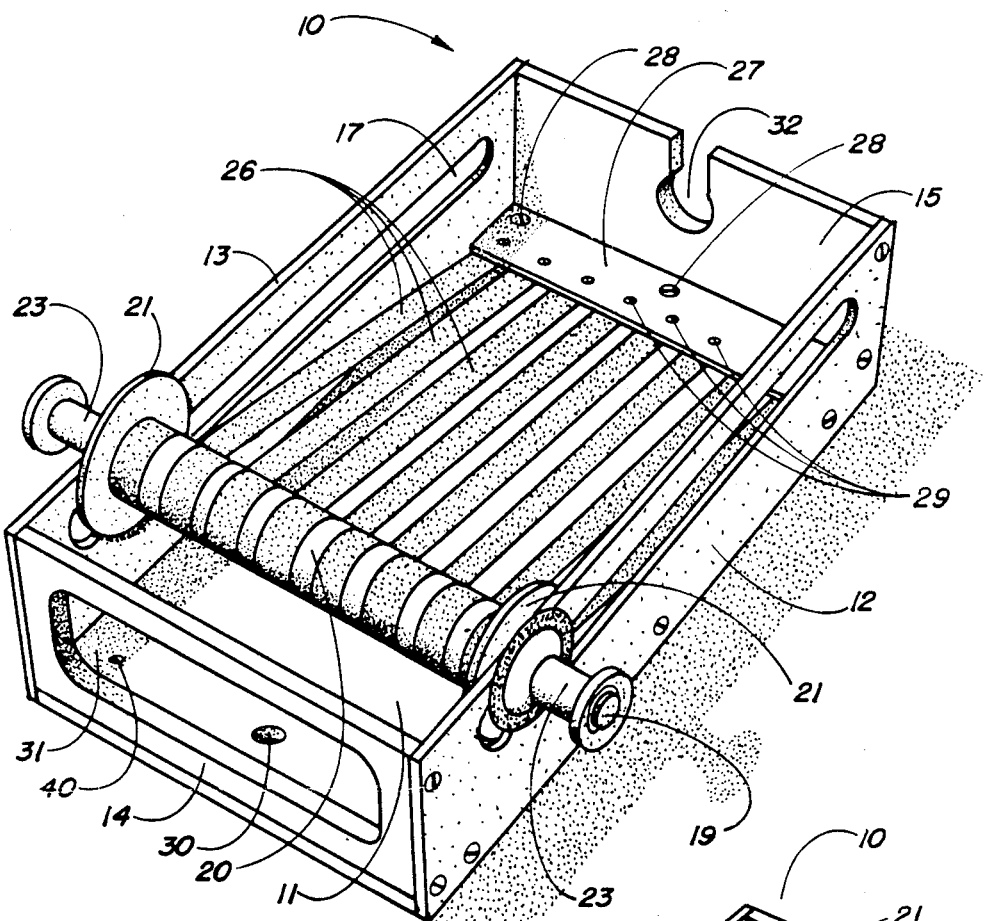
FIG. 3 is a top plan view of the improved infusion means of the present invention in cocked position.
FIG. 4 is top plan view of the improved infusion means of the present invention with the infusion bag disposed therein.

Next, the take-up drum 20 is pulled back by manipulating handles 23 to the position shown in FIG. 3 which is adjacent angulated offset slots 18. Still manipulating handles 23, the draw bar is moved upwardly into engagement with last mentioned slots. The handles 23 can then be released and the take-up drum 20 will remain in relative fixed position due to the constant tension of springs 26.

Next, infusion bag means which in the illustrated embodiment takes the form of a conventional infusion bag 34 is laid on springs 26 and the end opposite neck 33 is tucked into the spirals of the coil springs on take up drum 20. The neck 33 of the infusion bag is squeezed and slipped down into the bulbous end of slot 32. Because of this bulbous portion, such neck will be held in place thereby during use without need for a separate clamp.

Next, the cocking handles 23 are used to disengage the draw bar 19 from the angulated offset slots 18 and to place such draw bar in guide slots 27. The coiling pressure of constant tension springs 26 will cause a predetermined pressure to be developed within the infusion bag.

Figure 5:
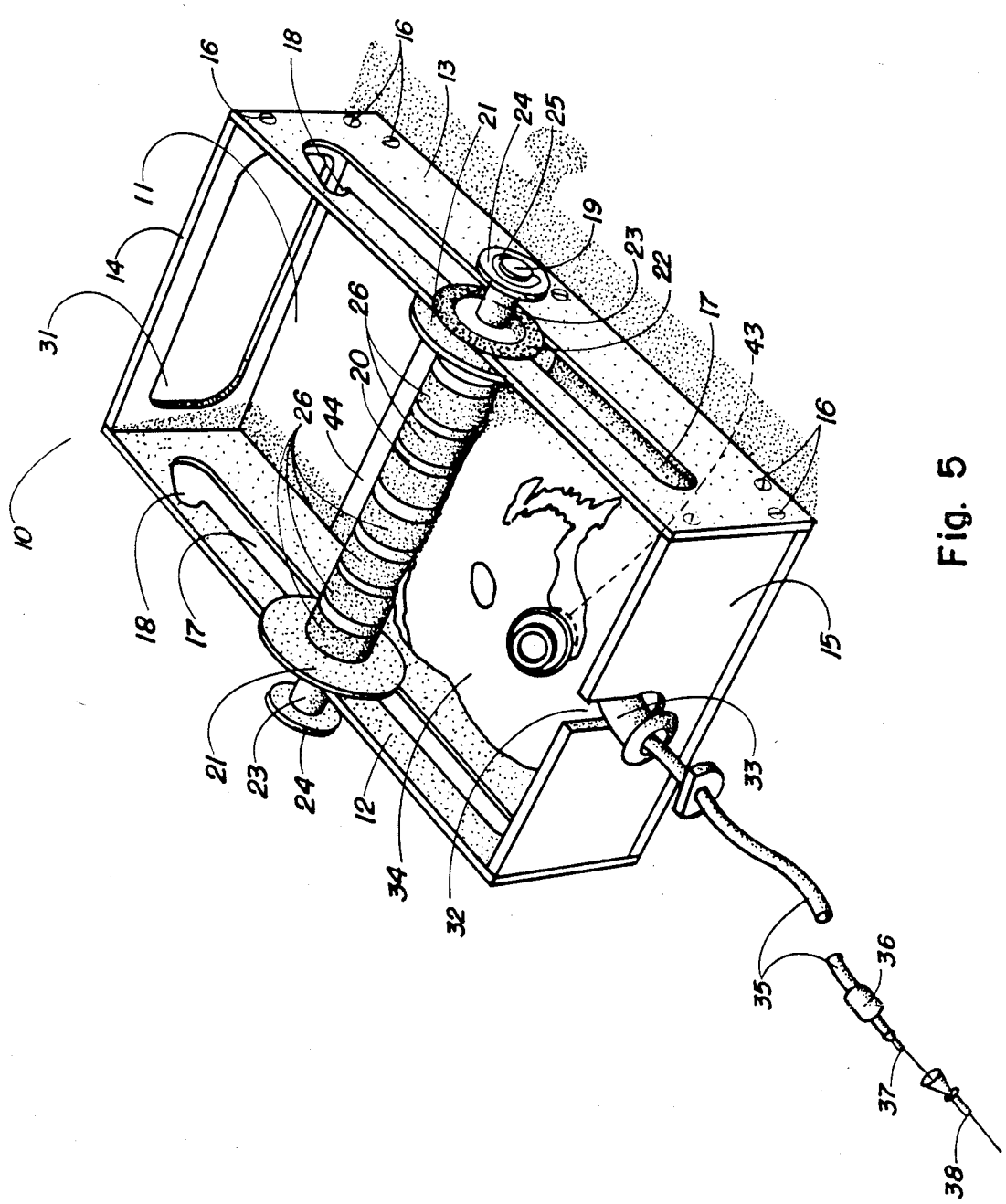
FIG. 5 is a top plan view of the improved infusion means of the present invention in actual operation.

The infusion needle 38 can then be inserted into the arm 41' of the patient 41 in the normal manner, the proper flow regulating needle 37, having already been selected and inserted as hereinabove described. It will be noted that when currently available intravenous infusion systems are used, it is standard practice to place the needle which is provided with the IV administration set within the vein. This method can certainly be employed with the present invention by using the flow regulating needle as the primary infusion needle. However, it is suggested, in cases where it is anticipated that more than one infusion bag will be needed, that an infusion needle be inserted into the patient, with the flow regulating needle being piggy-backed therein as shown in FIG. 5. In the manner of IV administration just described it is possible to avoid sticking the patient with more than one needle.

The clamp 36 can then be released thereby through the constant pressure created by the constant tension springs 26 and the flow being regulated by the flow regulating needle 37, a predetermined amount of liquid contained within infusion bag 34 can be infused into the patient 41 at a predetermined rate. In addition, the presence of end 15 serves as an abutment to aid in fully expelling the liquid from the infusion bag.

To prevent coagulation of blood in the area of the oriface of the infusion needle 38 proximate the vein when the flow from bag 34 slows or ceases due to the take-up drum 20 having been pulled by the constant tension springs 26 to a point adjacent end 15 of the improved infusion means 10 of the present invention, a small rupturable capsule or pouch 43 is provided interiorly of infusion bag 34. This capsule 34 will be compressed and ruptured as the take-up drum approaches end 15 of the present invention. An anticoagulant such as heparin is contained within the capsule or pouch and once the same has ruptured, will pass through the infusion tube 35, and flow in infusion needles 37 and 38 to prevent blood coagulation for an extended period of time. Once it becomes convenient, or the fact that the infusion bag is empty has been noticed, the same can be replaced as hereinabove described and flow will continue into the patient without having to re-establish communication with the interior of the vein of the patient by the infusion needle 38.

Further, different colored stripes such as that indicated at 44 can be provided on bottom 11 to form a visual alarm system. An example of this would be, as long as only green is visible the infusion bag 34 has sufficient of fluid left therein. As it approaches end 15, a yellow warning stripe would become visible, and as it approaches adjacent end 15, a red stripe would also be visible as a warning that the bag needed changing.

In summary, the improved infusion means of the present invention gives a constant predetermined flow rate at all times during dispensing of fluids from the infusion bag 34 as a result of the infusion pump being mounted in a predetermined relationship to the heart of the patient, a predetermined needle orifice size which regulates the flow from infusion tube 35, and the constant pressure placed on take up drum 25 by constant tension springs 26.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended Claims are intended to be embraced therein.

That which is claimed is:

1. An improved infusion means comprising:
   a frame means having guide means associated therewith;
   a take-up drum means operatively associated with said guide means;
   at least one coil type constant tension spring means secured at one end to said frame means and unsecuringly wound about said take-up drum at its opposite end;
   an infusion bag means containing a fluid disposed in contacting relation with and at least partially between the coils of said spring means adjacent said drum means;
   an infusion tube communicatively connected to said infusion bag;
   a fixed orifice flow regulating means operatively associated with said infusion tube; and
   wherein said spring means has a preselected spring constant such that said spring means applies a force to the infusion bag means to induce a pressure therein which is at least sufficient to overcome the venous back pressure thereby infusing the fluid into the vein, but is less than the force required to infuse a substantial amount of the fluid into the surrounding body tissue should the flow regulating means become dislodged from the vein and come to rest in the surrounding body tissue.

2. The infusion means of claim 1 wherein said flow regulating means is a fixed orifice smooth bore.

3. The infusion means of claim 1 wherein said flow regulating needle is changeable to vary the fluid flow rate.

4. The infusion means of claim 1 wherein said flow regulating means is a changeable flow regulating needle.

5. The infusion means of claim 1 wherein a means for dispensing an anticoagulant into said infusion tube is provided.

6. The infusion means of claim 5 wherein said means for dispensing an anticoagulant is a rupturable pouch contained within said infusion bag.

7. The infusion means of claim 6 wherein said pouch is ruptured by said infusion bag being wound between the coils of said constant tension spring means on said take-up drum.

8. A method of infusing a liquid into a patient comprising:
   placing an infusion bag under the coils of a constant tension spring unsecuringly wound on a take-up drum;
   placing an infusion tube in one end of said infusion bag;
   placing a flow regulating orifice of a predetermined size in said infusion tube;
   inserting said flow regulating orifice into the vein of said patient; and
   allowing said constant tension spring to wind up on said infusion bag and wherein the spring has a preselected spring constant such that the spring applies a force to the infusion bag to create a constant predetermined interior pressure therein which is at least sufficient to overcome the venous back pressure thereby infusing the liquid into the vein, but is less than the force required to infuse a substantial amount of the liquid into the surrounding body tissue should the flow regulating orifice become dislodged from the vein and come to rest in the surrounding tissue.

9. The method of claim 8 wherein said flow regulating orifice is in the form of a fixed orifice smooth bore flow regulating needle.

10. The method of claim 8 wherein said flow regulating orifice can be changed to vary the flow rate of fluid from said infusion bag into said patient.

11. The method of claim 8 wherein said infusion bag is mounted at a predetermined location relative to the heart of the patient.

12. An infusion means adapted to hold an infusion bag containing a fluid and wherein the infusion bag has connected to it an infusion tube, the other end of the infusion tube being connected to a fixed orifice needle which is inserted into the vein of a patient and comprising:
   a frame means having guide means associated therewith;
   a take-up drum means operatively associated with said guide means;
   at least one coil type constant tension spring means secured at one end to said frame means and unsecuringly wound about said take-up drum at its opposite end; and
   wherein said spring means has a preselected spring constant such that said spring means applies a force to the infusion bag to induce a pressure therein when the infusion bag is disposed in said frame means at least partially in contacting relation between the coils of said spring means and wherein the force induced is at least sufficient to overcome the venous back pressure thereby infusing the fluid into the vein, but is less than the force required to infuse a substantial amount of the fluid into the surrounding body tissue should the fixed orifice needle become dislodged from the vein and come to rest in the surrounding body tissue.

13. An infusion means according to claim 12 wherein said frame means further includes an end panel proximate the secured end of said constant tension spring means, whereby the fluid is more fully expelled from the bag as the constant tension spring means contracts.

14. An infusion means according to claim 12 wherein said end panel includes a notch means for facilitating insertion and removal of the infusion bag into and out of said frame.

* * * * *